United States Patent
Wang

(10) Patent No.: US 9,380,586 B2
(45) Date of Patent: Jun. 28, 2016

(54) MBAN CHANNEL USE REGULATION SCHEME AND ADAPTIVE CHANNELIZATION FOR IEEE 802.15.4J STANDARDIZATION

(75) Inventor: Dong Wang, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 33 days.

(21) Appl. No.: 14/114,543

(22) PCT Filed: Apr. 27, 2012

(86) PCT No.: PCT/IB2012/052110
§ 371 (c)(1),
(2), (4) Date: Oct. 29, 2013

(87) PCT Pub. No.: WO2012/150534
PCT Pub. Date: Nov. 8, 2012

(65) Prior Publication Data
US 2014/0065972 A1    Mar. 6, 2014

Related U.S. Application Data

(60) Provisional application No. 61/481,441, filed on May 2, 2011, provisional application No. 61/578,476, filed on Dec. 21, 2011.

(51) Int. Cl.
H04W 16/14    (2009.01)
H04W 72/04    (2009.01)
(Continued)

(52) U.S. Cl.
CPC ........... *H04W 72/0493* (2013.01); *A61B 5/002* (2013.01); *A61B 5/0024* (2013.01);
(Continued)

(58) Field of Classification Search
CPC ...................................................... H04L 67/12
See application file for complete search history.

(56) References Cited

U.S. PATENT DOCUMENTS 7,949,404 B2    5/2011  Hill
2006/0092907 A1    5/2006  Shimokawa et al.
(Continued)

FOREIGN PATENT DOCUMENTS

JP    2009507435         2/2009
WO    2006102538 A2     9/2006
(Continued)

OTHER PUBLICATIONS

NPL Jul. 2008—FCC-public-notice-David Davenport.*
(Continued)

*Primary Examiner* — Cindy Trandai

(57) ABSTRACT

A medical system includes one or more medical body area network (MBAN) systems. Each MBAN system includes one or more MBAN devices which acquire and communicate patient data with a hub device via short-range wireless communication. The communication of the patient data via the short-range wireless communication is within a predefined spectrum. The hub device receives patient data communicated from the one or more MBAN devices and communicates with a central monitoring station via a longer range communication. A MBAN channelization scheme defines one or more overlapping channels in the predefined spectrum and a MAC parameter dynamically enables or disables access to each defined channel. A channel regulator manages the MBAN utilization of the predefined spectrum by setting the MAC parameter to dynamically enable/disable the one or more predefined MBAN channels within the predefined spectrum.

19 Claims, 4 Drawing Sheets

Figure 1:
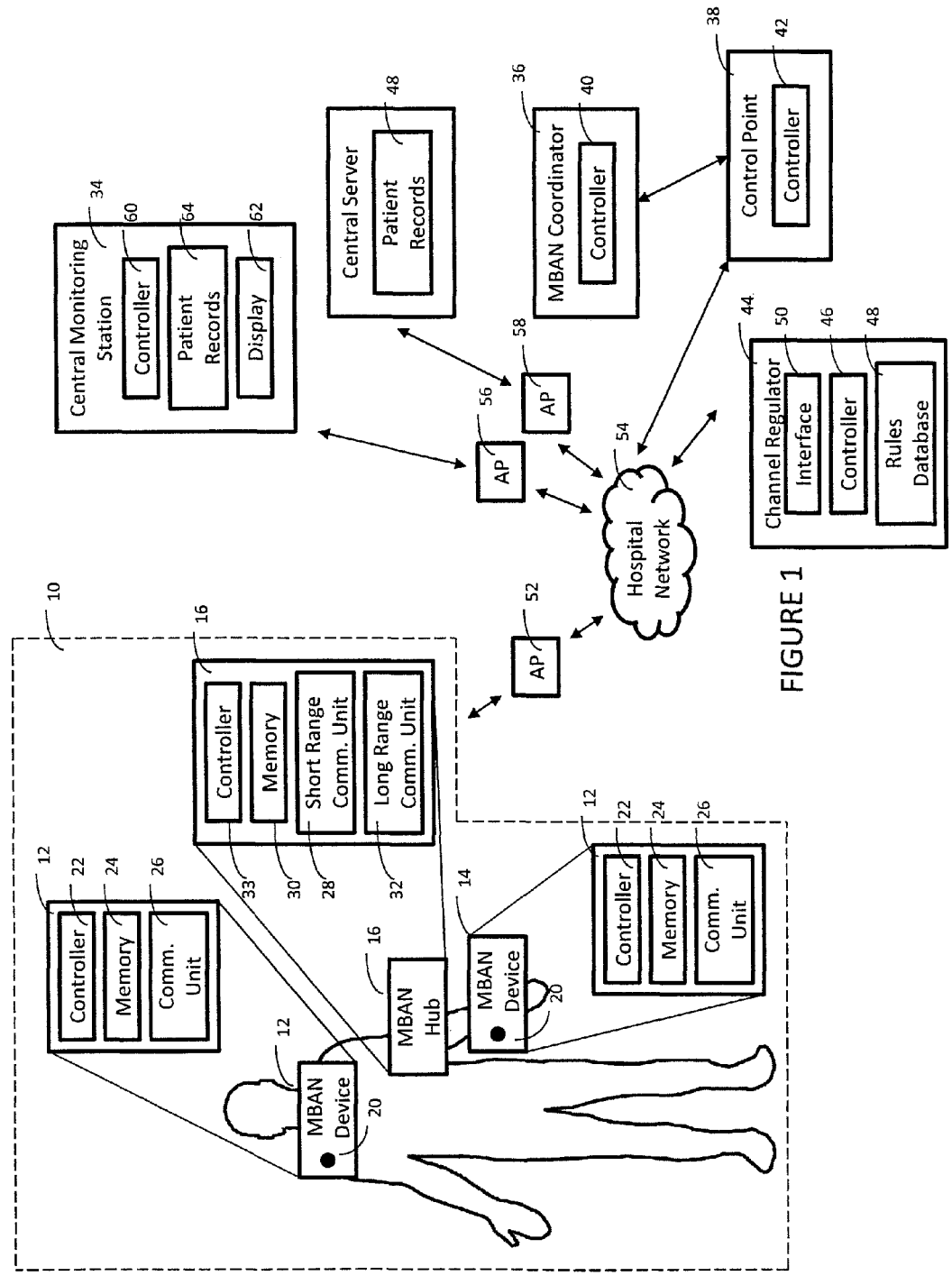

(51) Int. Cl.
| | |
|---|---|
| *A61B 5/00* | (2006.01) |
| *A61B 5/0205* | (2006.01) |
| *H04W 4/00* | (2009.01) |
| *A61B 5/024* | (2006.01) |
| *A61B 5/0402* | (2006.01) |
| *A61B 5/08* | (2006.01) |
| *A61B 5/145* | (2006.01) |
| *H04W 84/18* | (2009.01) |
| *G06F 19/00* | (2011.01) |

(52) U.S. Cl.
CPC ........... *A61B5/02055* (2013.01); *H04W 4/008* (2013.01); *H04W 16/14* (2013.01); *A61B 5/024* (2013.01); *A61B 5/0402* (2013.01); *A61B 5/0816* (2013.01); *A61B 5/14532* (2013.01); *A61B 5/4839* (2013.01); *G06F 19/3418* (2013.01); *H04W 84/18* (2013.01)

(56) References Cited

U.S. PATENT DOCUMENTS

2006/0251256 A1\* 11/2006 Asokan ................. H04L 63/065
                                                                 380/270
2007/0251835 A1   11/2007 Mehta et al.
2009/0310548 A1\* 12/2009 Kwon et al. ................... 370/329
2010/0075704 A1\*  3/2010 McHenry et al. ............. 455/509
2010/0261429 A1   10/2010 Batra et al.
2010/0315225 A1\* 12/2010 Teague .................... 340/539.12
2011/0294491 A1\* 12/2011 Fong et al. ................. 455/422.1

FOREIGN PATENT DOCUMENTS

WO    2010013164 A1    2/2010
WO    2011128795 A1    10/2011

OTHER PUBLICATIONS

Phillips Healthcare System (Oct. 5, 2009).\*
NPL Jul. 2008—FCC-public-notice-2360-to-2400-mhz-mbans-proposal-update.\*
Chen, S-L, et al.; Wireless Body Sensor Network with Adaptive Low-Power Design for Biometrics and Healthcare Applications; 2009; IEEE Systems Journal; 3(4)398-409.
Smith, D.; Comments of Philips Healthcare Systems; Amendment of the Commission's Rules to Provide Spectrum for the Operation of Medical Body Area Networks; 2009; pp. 1-67.
Wang, J., et al.; Emerging Cognitive Radio Applications: A Survey; 2011; IEEE Communications Magazine; 49(3) 74-81.

\* cited by examiner

MBAN CHANNEL USE REGULATION SCHEME AND ADAPTIVE CHANNELIZATION FOR IEEE 802.15.4J STANDARDIZATION

CROSS REFERENCE TO RELATED APPLICATIONS

This application is a national filing of PCI application Serial No. PCT/IB2012/052110, filed Apr. 27, 2012, published as WO 2012/150534 A1 on Nov. 8, 2012, which claims the benefit of U.S. provisional application Ser. No. 61/481,441 filed May 2, 2011 and U.S. provisional application Ser. No. 61/578,476 filed Dec. 21, 2011, both of which are incorporated herein by reference.

The present application relates to medical monitoring and clinical data devices for monitoring the physiological condition of a patient. It finds particular application in the use of a channelization scheme and channel use regulation for IEEE 82.15.4j standardization.

The rapid growth in physiological sensors, low power integrated circuits, and wireless communication has enabled a new generation of medical body area networks (MBAN) to be used to monitor patients. MBANs provide low-cost wireless patient monitoring (PM) without the inconvenience and safety hazards posed by wired connections, which can trip medical personnel or can become detached so as to lose medical data. In the MBAN approach, multiple low cost sensors are attached at different locations on or around a patient. These sensors take readings of patient physiological information such as patient temperature, pulse, blood glucose level, electrocardiographic (ECG) data, or so forth. The sensors are coordinated by at least one proximate hub or gateway device to form the MBAN. The hub or gateway device communicates with the sensors using embedded short-range wireless communication radios, for example, conforming with an IEEE 802.15.4 (Zigbee) short-range wireless communication protocol. Information collected by the sensors is transmitted to the hub or gateway device through the short-range wireless communication of the MBAN, thus eliminating the need for wired connections. The hub or gateway device communicates the collected patient data to a central patient monitoring station via a wired or longer-range wireless link for centralized processing, display and storage. The longer-range network may, for example, include wired Ethernet and/or a wireless protocol such as Wi-Fi or some proprietary wireless network protocol. The PM station may, for example, include an electronic patient record database, display devices located at a nurse's station or elsewhere in the medical facility, or so forth.

MBAN monitoring acquires patient physiological parameters. Depending upon the type of parameter and the state of the patient, the acquired data may range from important (for example, in the case of monitoring of a healthy patient undergoing a fitness regimen) to life critical (for example, in the case of a critically ill patient in an intensive care unit). Because of this there is a strict reliability requirement on the MBAN wireless links due to the medical content of the data. However, the current spectrum allocations and regulations for medical wireless connectivity do not meet the strict requirements of MBAN, including medical-grade link robustness, ultra low-power consumption, and low-cost, due to either limited bandwidth or uncontrolled interference.

Frequency spectrum regulation policies try to increase the spectrum use efficiency. One way to increase efficiency is to allocate an opportunistic spectrum specifically for MBAN applications and services as secondary users of a spectrum that has been previously allocated to other services on a primary basis. The basic idea of an opportunistic spectrum is to allow secondary users to opportunistically utilize the spectrum that has been previously allocated to primary users as long as such secondary users do not introduce harmful interference to the primary users. For example, it has been proposed in the U.S. to open the 2360-2400 MHz band (MBAN spectrum), currently assigned to others, to MBAN services as a secondary user. Similar proposals have been made or are expected to be made in other countries. The wide bandwidth, interference-free, and good propagation properties of the MBAN spectrum would meet the strict requirements for medical-grade connectivity. In order to achieve co-existence between primary users and secondary users, some restrictions (or spectrum regulation rulings) would be put on the spectrum use of secondary users.

For example, when the allocated MBAN spectrum is used on a secondary basis, the secondary user would have to protect the primary users in that spectrum. For example, to protect the primary users, secondary users are often required to provide appropriate mechanisms to vacate the spectrum of the primary user when the primary user wants to use the spectrum. To accomplish this, enforcement mechanisms are needed. The present application proposes a channel use regulation scheme for MBAN systems to guarantee compliance with the MBAN regulations.

A conventional channelization scheme would define multiple non-overlapping channels in the MBAN spectrum. For example, a channelization scheme for an IEEE 802.15.4j (15.4j) communication standard could define multiple fixed non-overlapping channels in the 2360-2400 MHz band. Since an IEEE 802.15.4j (15.4j) radio has a channel bandwidth of 5 MHz with guard bands at band edges to meet out-of-band-emission (DOBE) limits, then at most, 7 non-overlapping channels could be defined in the 2360-2400 MHz band. For example, 7 channels are defined with a central frequency at 2363, 2368, 2373, 2378, 2383, 2388, and 2395 MHz, respectively. Since the central frequencies of those channels (in MHz) are integers and thus align with the channel central frequencies already defined with an already preexisting IEEE 802.15.6 (15.6) standard, no 15.6 channel straddles two 15.4j channels. Moreover, the guard bands are fixed (2360-2360.5, 2390.5-2392.5, 2397.5-2400 MHz), so 15.6 radios can choose the 15.6 channels within those guard bands (e.g. 15.6 channels centered at 2391, 2392, 2398, and 2399 MHz) to operate to avoid potential mutual interference with 15.4j systems.

However, there are some severe drawbacks about this simple channelization scheme. First, there is only one channel defined in the 2390-2400 MHz band. This means for remote monitoring applications deployed outside hospitals, there is only one channel available for 15.4j radio operations. If there exists an amateur radio operating nearby in the 2396-2399 MHz band (e.g. high-rate data mode amateur), then no interference free channel is available for 15.4j radios. Therefore, the simple channelization scheme can't use the spectrum efficiently because the amateur radio only utilizes a 3 MHz spectrum and there is still a 7 MHz idle spectrum available for 15.4j operation.

Furthermore, such simple channelization scheme may not be able to use the spectrum efficiently when there is portion of spectrum to be protected for primary users. For example, if the MBAN coordinator concludes that a hospital has to avoid using the 2370-2382 MHz spectrum since such spectrum is currently used by primary users, then there are only 3 channels available for that hospital to deploy 15.4j MBAN devices. The simple channelization scheme only uses 15 MHz spectrum (3 channels each with 5 MHz bandwidth) even there are 28 MHz spectrum available in the 2360-2390 MHz band. Such low spectral use efficiency might not be acceptable in some cases. Additionally, some mechanism is needed to regulate the use of 15.4j channels to protect primary users. For example, in the above example, there should be some mechanism to notify MBAN devices that Channel 1, 2, 3 and 4 are prohibited.

The present application provides a new and improved system and method for MBAN channel use regulation and adaptive channelization which overcomes the above-referenced problems and others.

In accordance with one aspect, a medical system is provided. The medical system includes one or more medical body area network (MBAN) systems. Each MBAN system includes one or more MBAN devices which acquire and communicate patient data with a hub device via short-range wireless communication. The communication of the patient data via the short-range wireless communication being within a predefined spectrum. The hub device receives patient data communicated from the one or more MBAN devices and communicates with a central monitoring station via a longer range communication. A channel regulator manages the MBAN utilization of the predefined spectrum.

In accordance with another aspect, a method is provided. The method including collecting patient data by one or more medical body area network (MBAN) devices, prohibiting one or more MBAN devices from utilizing at least a portion of a predefined spectrum, communicating the collected patient data from the one or more MBAN devices through a MBAN system to a hub device via short-range wireless communication, the communication via short-range wireless communication within a predefined spectrum, and communicating the collected patient data from the hub device to a central monitoring station via longer range wireless communication.

In accordance with another aspect, a method is provided. The method including collecting patient data by one or more medical body area network (MBAN) devices, prohibiting the one or more MBAN devices from utilizing at least a portion of a predefined spectrum, part of the predefined spectrum being in use by a primary user and unavailable for use, defining a channelization scheme with one or more channels of the predefined spectrum accessible to the one or more MBAN devices, the channelization scheme maximizing a number of channels in one or more portions of the spectrum not in use by the primary user, and communicating the collected patient data from the one or more MBAN devices through a MBAN system to a hub device via short-range wireless communication, wherein the communication via short-range wireless communication within a predefined spectrum.

One advantage resides in the efficient utilization of a MBAN spectrum using adaptive channelization and channel use regulation.

Another advantage resides in the compliance with MBAN regulations.

Another advantage resides in the coexistence with primary users of a spectrum and other MBAN devices.

Another advantage resides in improved healthcare workflow efficiency, safety, and clinical outcome.

Still further advantages of the present invention will be appreciated to those of ordinary skill in the art upon reading and understand the following detailed description.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically illustrates a medical body area network (MBAN) system in accordance with the present application.

Figure 2:
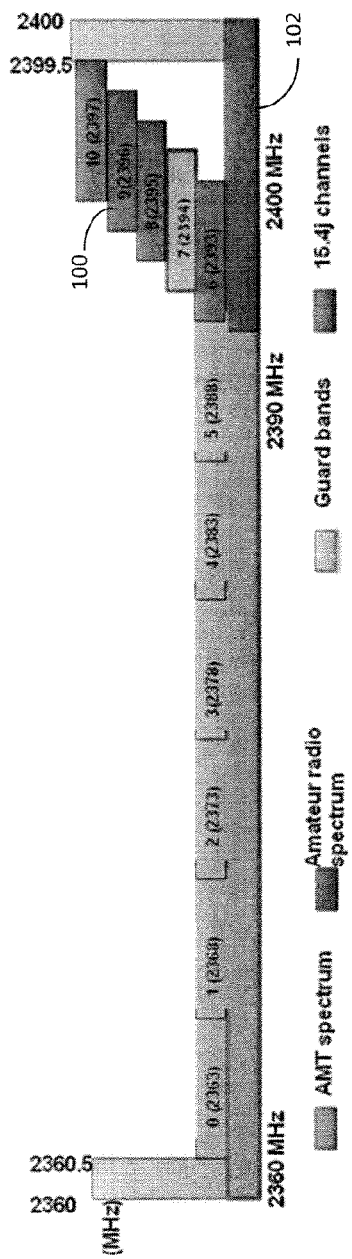

FIG. 2 diagrammatically illustrates a channelization scheme of the MBAN system in accordance with the present application.

Figure 3:
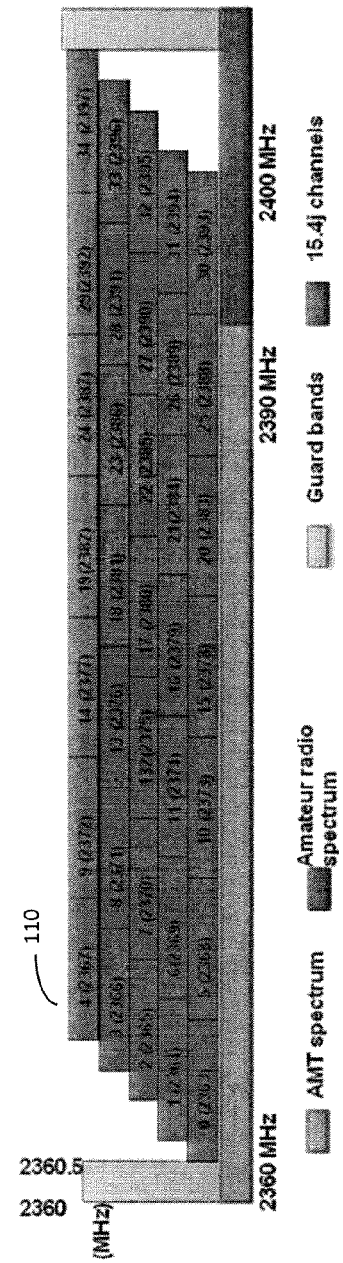

FIG. 3 diagrammatically illustrates another channelization scheme of the MBAN system in accordance with the present application.

Figure 4:
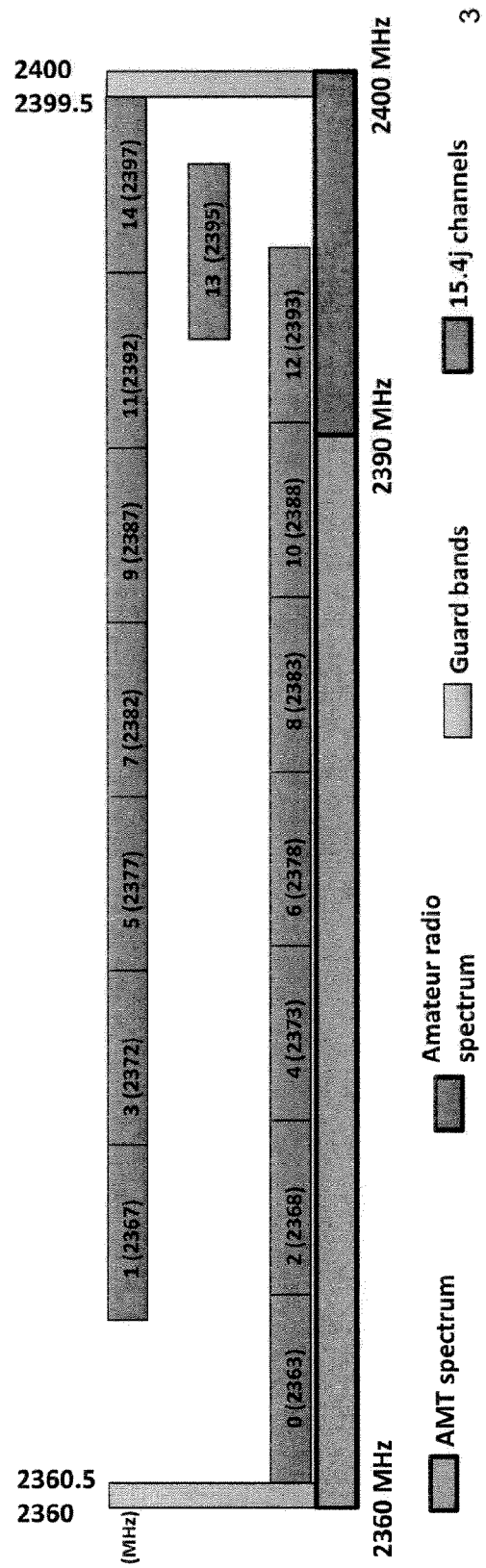

FIG. 4 diagrammatically illustrates another channelization scheme of the MBAN system in accordance with the present application.

Figure 5:
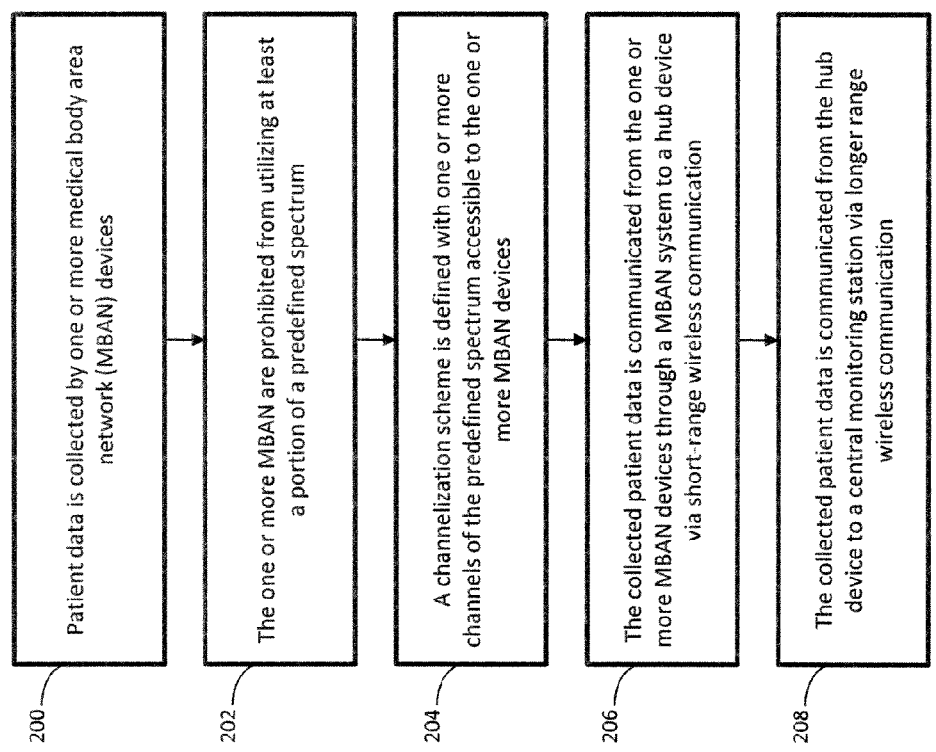

FIG. 5 is a flowchart diagram of the operation of the MBAN system in accordance with the present application.

FIG. 1 illustrates a medical body area network (MBAN) 10 which implements a channelization scheme and channel use regulation for IEEE 802.15.4j standardization. In a first channelization scheme, non-overlapping channels are defined in a MBAN spectrum, which can only be accessed within a healthcare facility upon coordination, while overlapping channels are defined in a first portion of the MBAN spectrum, which can be accessed anywhere. Fixed non-overlapping channels defined in a second portion of the MBAN spectrum would simplify implementation and promote coexistence with other in-band MBAN users, such as IEEE 802.15.6 radios and the like, within healthcare facilities. At the same time, overlapping channels defined in the first portion of the MBAN spectrum provide flexibility for out-of-hospital MBAN applications to mitigate mutual interference with other users in the second portion of the MBAN spectrum. A second channelization scheme improves spectral use efficiency in the cases where MBAN systems need to protect primary users' spectrum in the first portion of the MBAN spectrum. A third channelization scheme simplifies the second channelization scheme by defining fewer channels in the MBAN spectrum, which can provide a good tradeoff between spectral use efficiency and implementation complexity. In the latter two cases, overlapping channels are defined in the whole MBAN spectrum to provide more channel choices for MBAN operations. To avoid the use of overlapping channels in healthcare facilities, a new MAC channel mask parameter is introduced to dynamically enable/disable the use of each defined channels. The primitive to set the channel mask parameter ensures that only non-overlapping channels can be enabled within the first portion of the MBAN spectrum such that using overlapping channels in a healthcare facility is prohibited. Non-overlapping channels to be used in a healthcare facility can be dynamically changed to adapt to its spectrum situation. Overlapping channels are allowed in the second portion of the MBAN spectrum to promote coexistence in remote monitoring scenarios. The channel use regulation includes an MBAN regulator which interfaces to an MBAN coordinator and other MBAN devices and is responsible for generating channel use rules for each type of MBAN device based on the E-key/authorization received from the MBAN coordinator and the spectrum use status of other MBAN devices.

With reference to FIG. 1, each medical body area network (MBAN) 10 of a plurality of MBANs includes a plurality of MBAN devices 12, 14 and a corresponding hub device 16. The MBAN devices 12, 14 communicate with the corresponding hub device 16 via a short-range wireless communication protocol. The MBAN 10 is also sometimes referred to in the relevant literature by other equivalent terms, such as a body area network (BAN), a body sensor network (BSN), a personal area network (PAN), a mobile ad hoc network (MANET), or so forth the term medical body area network (MBAN) 10 is to be understood as encompassing these various alternative terms.

The illustrative MBANs 10 includes two illustrative MBAN devices 12, 14 and a corresponding hub devices 16; however, the number of MBAN devices and hub devices can be one, two, three, four, five, six, or more, and moreover the number of MBAN devices may in some embodiments increase or decrease in an ad hoc fashion as MBAN devices are added or removed from the network to add or remove medical monitoring capability. The MBAN devices 12, 14 include one or more sensors 20 that acquire patient data including physiological parameters such as heart rate, respiration rate, electrocardiographic (ECG) data, or so forth; however, it is also contemplated for one or more of the MBAN devices to perform other functions such as controlled delivery of a therapeutic drug via a skin patch or intravenous connection, performing cardiac pacemaking functionality, or so forth. Other MBAN devices can be associated with a patient, and not all of the above-mentioned MBAN devices have to be associated with a patient at any given time. A single MBAN device may perform one or more functions. The illustrative MBAN devices 12, 14 are disposed on the exterior of an associated patient; however, more generally the MBAN devices may be disposed on the patient, or in the patient (for example, a MBAN device may take the form of an implanted device), or proximate to the patient within the communication range of the short-range communication protocol (for example, a MBAN device may take the form of a device mounted on an intravenous infusion pump (not shown) mounted on a pole that is kept near the patient, and in this case the monitored patient data may include information such as the intravenous fluid flow rate). It is sometimes desirable for the MBAN devices to be made as small as practicable to promote patient comfort, and to be of low complexity to enhance reliability accordingly, such MBAN devices 12, 14 are typically low-power devices (to keep the battery or other electrical power supply small) and may have limited on-board data storage or data buffering. As a consequence, the MBAN devices 12, 14 should be in continuous or nearly continuous short-range wireless communication with the corresponding hub device 16 in order to expeditiously convey acquired patient data to the corresponding hub device 16 without overflowing its data buffer.

In FIG. 1, the short-range wireless communication range is diagrammatically indicated by the dotted line used to delineate the MBAN system 10. The short-range wireless communication is typically two-way, so that the MBAN devices 12, 14 can communicate information (e.g., patient data, MBAN device status, or so forth) to the corresponding hub device 16; and the corresponding hub device 16 can communicate information (e.g., commands, control data in the case of a therapeutic MBAN device, or so forth) to the MBAN devices 12, 14. The illustrative hub device is a waist-mounted device which facilitates carrying a longer, heavier battery and other hardware for longer range transmissions; however, the hub device can be otherwise mounted to the patient, for example as a wrist device, adhesively glued device, or so forth. It is also contemplated for the hub device to be mounted elsewhere proximate to the patent, such as being integrated with an intravenous infusion pump (not shown) mounted on a pole that is kept near the patient.

The patient data acquired from the sensors 20 is concurrently transmitted to a controller 22 in the corresponding MBAN device. The MBAN devices 12, 14 serve as a gathering point for the patient data acquired by the sensors 20 and provide temporary storage of the patient data in a memory 24. The MBAN devices 12, 14 also include a communication unit 26 for transmitting the patient data via short-range wireless communication protocol to the corresponding hub device 16. The communication unit 26 include a transceiver (not shown) to transmit the patient data and information, received by the controller 22, and receive information, from the hub device 16.

The short-range wireless communication protocol preferably has a relatively short operational range of a few tens of meters, a few meters, or less, and in some embodiments suitably employs an IEEE 802.15.4 (Zigbee) short-range wireless communication protocol or a variant thereof, or a Bluetooth™ short-range wireless communication protocol or a variant thereof. Although Bluetooth™ and Zigbee are suitable embodiments for the short-range wireless communication, other short-range communication protocols, including proprietary communication protocols, are also contemplated. The short-range communication protocol should have a sufficient range for the hub device 16 to communicate reliably with all MBAN devices 12, 14 of the MBAN system 10. The short-range wireless communication protocol between the MBAN devices 12, 14 and the corresponding hub device 16 and in some embodiments between MBAN devices operate in a frequency spectrum of around 2.3-2.5 GHz.

Due to the strict reliability requirements on MBAN system 10 communications because of the medical content of the patient data being transmitted, an opportunistic MBAN spectrum is specifically allocated for the communication of the patient data, for example, in the 2360-2400 MHz band discussed above. In the MBAN spectrum, the MBAN devices 12, 14 are secondary users of the spectrum or can use it on a secondary basis meaning the MBAN systems would have to yield to the primary users in that spectrum. To protect the primary user, the MBAN system 10 implements a channelization scheme and channel use regulation. In a first channelization scheme, non-overlapping channels are defined in the MBAN spectrum, which can only be accessed within a healthcare facility upon coordination, while overlapping channels are defined in a first portion of the MBAN spectrum, which can be accessed anywhere. Fixed non-overlapping channels defined in a second portion of the MBAN spectrum would simplify implementation and promote coexistence with other in-band MBAN users. In a second channelization scheme, spectral use efficiency is improved in the cases where MBAN systems need to protect primary users' spectrum in the first portion of the MBAN spectrum. Overlapping channels are defined in the whole MBAN spectrum to provide more channel choices for MBAN operations. To avoid the use of overlapping channels in healthcare facilities, a MAC parameter is introduced to dynamically enable/disable the use of each defined channels. The channel use regulation includes generating channel use rules for each type of MBAN device based on the E-key/authorization received from an MBAN coordinator and the spectrum use status of other MBAN devices. In a third channelization scheme, fewer overlapping channels are defined in the whole MBAN spectrum to provide a good tradeoff between spectral use efficiency and implementation complexity.

To accomplish this, healthcare facilities which want to access the MBAN spectrum are required to register with an assigned MBAN coordinator 36. The MBAN coordinator 36 performs MBAN coordination with the healthcare facilities and generates an E-key to authorize access to part or the whole of the MBAN spectrum to the healthcare facilities. Each registered healthcare facility deploys a single centralized control point device 38 that communicates with a controller 40 of the MBAN coordinator 36 and receives (either automatically via network connection or manually via Email, mail or other methods) the E-key. The issued E-key includes authorized frequencies and time period for MBAN operations. A controller 42 of the MBAN control point 38 receives and automatically conveys the E-key information to the MBAN systems 10 deployed within such facility to regulate their uses of the MBAN spectrum.

The healthcare facility also includes a MBAN channel regulator 44 which is used as an interface between the MBAN control point 38 and the MBAN systems 10. A controller 46 of the MBAN channel regulator 44 receives the E-Key information generated by the MBAN coordinator 36 and translates it into channel use rules for each type of MBAN system 10 within the healthcare facility that are stored in a MBAN rules database 48. The MBAN channel regulator 44 also interfaces to each type of MBAN systems, such as 15.4j radios, 15.6 radios, and other proprietary systems. The controller 46 of the MBAN channel regulator 44 forwards the corresponding channel uses rules to each type of MBAN system 10 to regulate their uses of the MBAN spectrum. The MBAN channel regulator 44 also provides a user interface 50 (via network connection or local connection) for hospital MBAN system administrators to customize those channel use rules. Additionally, each MBAN system 10 feedbacks their channel use information to the MBAN channel regulator 44. Based on channel use information, the MBAN regulator 44 generates the MBAN spectrum use report and forwards the report to MBAN control point 38 and MBAN coordinator 36 to monitor the MBAN spectrum use. Moreover, the MBAN channel regulator 44 has the channel use information of all deployed MBAN systems 10 and can use such information to optimize the channel use of each type of MBAN systems 10. For example, the MBAN channel regulator 44 can generate a prioritized channel list for each type of MBAN system to assist MBAN systems to select their operating channels.

For example, if the issued E-key indicates that only 2360-2370 and 2382-2390 MHz bands are authorized for MBAN operation (or in other words, the 2370-2382 MHz spectrum is in use by the primary users and should be protected) then the MBAN channel regulator 44 translates such E-key information into channel use rules that are forwarded to all MBAN systems 10 to prohibit the use of specific channels to protect the 2370-2382 MHz spectrum. The MBAN channel regulator 44 also generates channel rules based on its E-key information to enable certain channels for general MBAN use and enable other channels to be used for high priority MBAN use. For example, the MBAN channel regulator 44 may translate the E-key information into 15.4j channel use rules authorizing channels 0 (2363 MHz), 5 (2388 MHz), and 6 (2393 MHz) to be enabled while the other channels are disabled to ensure that 15.4j MBAN radios only use the authorized spectrum, assuming the first channelization scheme is adopted. Such rules are forwarded to all 15.4j MBAN systems to prohibit the use of channel 1, 2, 3, and 4 to protect the 2370-2382 MHz spectrum. If the hospital also deploys 802.15.6 based MBAN systems, the MBAN channel regulator 44 generates the channel rules based on its E-key information and the 15.4j channel use rules it maintains as channels 0, 1, . . . , 8, 22, 23, . . . , 37 and 38 are enabled and channels 22, 23, 24, 30, 31, 37 and 38 used with high priority. Channel 22, 23, 24, 30, 31, 37 and 38 have high priority because they are located within the gaps that the current 802.15.4 channel use rules prohibit 15.4j MBAN radios to access. Such 15.6 channel use rules promote 802.15.4j/802.15.6 coexistence performance.

Moreover, the MBAN administrator of the hospital can customize the MBAN spectrum planning by customizing the channel use rules for different areas within hospitals. Since MBAN systems usually connect to the healthcare facility IT network either via wireless access points or wired Ethernet port and the MBAN channel regulator 44 receives location information of wireless APs and Ethernet ports of healthcare IT networks, the MBAN administrator can customize MBAN channel use rules for wireless APs and Ethernet ports within specific areas to control MBAN spectrum use of MBAN systems associated with those APs and ports. For example, in an emergence room (ER) area, numerous patients could be wearing MBAN systems to monitor their physiological status. To support such high density deployment, the MBAN administrator may limit the number of enabled channels and reserve more spectrums for specific MBAN systems since some specific MBAN systems have a narrower channel and can provide more channels for operation. For example, if the E-key authorizes a hospital to access the whole 2360-2390 MHz band, instead of defining the channel use rules to enable all the channels defined, the MBAN administrator can customize the channel use rules for the ER area and only enable certain channels while enabling all the channels and giving the other channels high priority. These customized rules would provide sufficient channels for MBAN operations and promote coexistence between different types of MBAN devices.

The hub device 16 coordinates operation of its MBAN system 10 over the MBAN spectrum to receive the patient data acquired by the sensors 20 of the MBAN devices 12, 14 and transmits the collected patient data from the MBAN 10 via a longer range communication protocol to a central monitoring station 34. The patient data acquired from the sensors 20 is concurrently transmitted from the MBAN devices 12, 14 to a short range communication device 28 in the corresponding hub device 16. The hub device 16 serves as a gathering point for the patient data acquired by the sensors 20 of all the MBAN device 12, 14 in the MBAN network, e.g. all of the MBAN devices associated with one patient, and provides temporary storage of the patient data in a memory 30. The hub device 16 also includes a longer range communication unit 32 for transmitting the patient data via a longer range wireless communication protocol to the central monitoring station 34. A controller 33 of the MBAN hub 16 controls communication with the MBAN devices 12, 14, collection and handling of the patient data, retransmission of the patient data to a central monitoring station 34, receiving acknowledgements, setting up the network, associating new MBAN devices, disassociating removed MBAN devices, and the like.

The longer range communication unit 32 of the hub device 16 also includes a transceiver which provides the longer-range communication capability to communicate data from the MBAN system 10. In the illustrative example of FIG. 1, the hub device 16 wirelessly communicates with a central monitoring station 34 through an AP 52 of a hospital network 54. The illustrative AP 52 is a wireless access point that communicates wirelessly with the hub device 16. In the illustrative embodiment, the hospital network 54 also includes additional access points, such as illustrative access points AP 56 and AP 58 that are distributed throughout the hospital or other medical facility. To provide further illustration, a central monitoring station is diagrammatically indicated, which is in wireless communication with the AP 56. Different APs 52, 56-58 cover different areas of the healthcare facility and their coverage areas could overlap with each other to provide seamlessly roaming service.

To provide further illustration, the central monitoring station 34 includes a controller 60 for receiving the patient data from many hub devices. The central monitoring station 34 also includes a display monitor 62 that may, for example, be used to display medical data for the patient that are acquired by the MBAN system 10 and communicated to the central monitoring station 34 via the AP 56 of the hospital network 54. The central monitoring station 34 also communicates with an electronic patient records sub-system 64 in which patient data and records for all current and past patients is stored. Communication between the central monitoring stations and the electronic patient records sub-system 64 is communicated via APs 52, 56 of the hospital network 54. The longer-range wireless communication is suitably a WiFi communication link conforming with an IEEE 802.11 wireless communication protocol or a variant thereof. However, other wireless communication protocols can be used for the longer-range communication, such as another type of wireless medical telemetry system (WMTS). Moreover, the longer range communication can be a wired communication such as a wired Ethernet link (in which case the hospital networks include at least one cable providing the wired longer range communication link).

The longer range communication has longer range as compared with the short-ranger communication between the MBAN devices 12, 14 and the corresponding hub device 16. For example, the short-range communication range may be of order a meter, a few meters, or at most perhaps a few tens of meters. The longer range communication can be long enough to encompass a substantial portion or all of the hospital or other medical facility whether directly or via the plurality of APs to the hospital network.

The longer-range communication, if wireless, requires more power than the short-range communication. Accordingly, the hub device 16 includes a battery or other power source sufficient to operate the longer-range communication transceiver. The hub device 16 also typically includes sufficient on-board storage so that it can buffer a substantial amount of patient data in the event that communication with the hospital network 54 is interrupted for some time interval. In the illustrative case of wireless longer-range communication, it is also to be understood that if the patient moves within the hospital or healthcare facility then the IEEE 802.11 or other wireless communication protocol employed by the hospital network 54 provides for the wireless communication. In this regard, although the patient may be confined to a bed, more generally it is contemplated that the patient may be ambulatory and moving around the hospital or healthcare facility. As the patient moves, the MBAN system 10, including the MBAN devices 12, 14 and the hub device 16, move together with the patient.

In the MBAN system 10, the MBAN devices 12, 14 communicate with the hub device 16 via the short-range wireless communication. However, it is also contemplated for various pairs or groups of the MBAN devices 12, 14 to also intercommunicate directly (that is, without using the hub devices 16, 18 as an intermediary) via the short-range wireless communication. This may be useful, for example, to coordinate the activities of two or more MBAN devices in time. Moreover, the hub devices 16, 18 may provide additional functionality. For example, the hub devices 16, 18 may also be a MBAN device that includes one or more sensors for measuring physiological parameters. Still further, while the single hub devices 16, 18 is illustrated, it is contemplated that an MBAN system can have two or more hubs that cooperatively perform the task of coordinating functionality (e.g. data collection from the MBAN devices 12, 14 and offloading the collected data via the longer range wireless communication).

In illustrative FIG. 1, only one MBAN system 10 is illustrated in detail. However, it will be appreciated that more generally the hospital or other medical facility includes a plurality of patients, each having his or her own MBAN system. More generally, the number of MBAN systems may be, by way of some illustrative examples: the hundreds, thousands, tens of thousands, or more depending on the size of the medical facility. Indeed, it is even contemplated for a single patient to have two or more different, independently or cooperatively operating MBAN systems (not illustrated). In this environment, various MBAN systems of different patients can be expected to come into close proximity with one another, such that the ranges of the respective MBAN system short-range wireless communications overlap.

The MBAN devices 12, 14, the MBAN hub 16, the MBAN system 10, the MBAN coordinator 36, the MBAN control point 38, the MBAN channel regulator 44, and the central monitoring station 34 in the illustrative embodiment include at least one processor, for example a microprocessor or other software controlled device configured to execute MBAN software for performing the operations described in further detail below. Typically, the MBAN software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

With reference to FIG. 2, a first channelization scheme utilizing overlapping channels in the MBAN spectrum is illustrated. The first channelization scheme avoids strong adjacent channel interference caused by the use of overlapping channels in such a spectrum by defining fixed non-overlapping channels in a second portion of the MBAN spectrum, which can only be accessed within a healthcare facility. This is important for in-healthcare-facility deployment in-healthcare-facility deployment has higher MBAN system density and adjacent channel interference is likely to happen. This channelization scheme along with the system architecture regulates the use of MBAN spectrum channels. Specifically, the upper layer protocol (e.g. network layer protocol or application layer protocol) of the MBAN hub device defines a new channel mask parameter, ChannelEnabled, which dynamically enable/disable access to each defined MBAN channel. For example, by default, ChannelEnabled is set to only enable channels 6-10 100, which are inside the MBAN spectrum band 102. This would allow MBAN devices to access enabled channels inside the MBAN spectrum band anywhere (i.e. inside healthcare facility and outside healthcare facility). Once an MBAN hub device establishes a valid connection to the healthcare IT network of a healthcare facility, it can obtain the channel use rules from its backhaul access point (AP) device (when via wireless link) or from the channel regulator directly (when via wired port connection) and set its ChannelEnabled accordingly. It broadcasts this parameter to other MBAN devices associated with its network. The MBAN hub device only selects an enabled channel to operate. Once an MBAN hub device lose its connection to the healthcare IT network, its ChannelEnabled parameter resets to its default value that only enables specified channels.

In the first channelization scheme, the central frequencies of non-overlapping channels are fixed in the MBAN spectrum band and limit MBAN systems to use the spectrum efficiently when there is portion of a primary user spectrum to be protected. In order to solve this problem, a second channelization scheme utilizes overlapping channels with channel steps defined in the MBAN spectrum band and a new parameter, MacChannelEnabled, included in the MAC layer protocol to dynamically enable/disable those overlapping channels. The second channelization scheme is illustrated in FIG. 3 in which 35 overlapping channels 110 are defined with a channel step of 1 MHz.

The MAC layer provides a primitive/service call MLME-Set to the upper layer protocol to set the parameter MacChannelEnabled. The MLME-Set primitive checks if the input value of MacChannelEnabled from the upper layer is a valid one, in terms of if it enables overlapping channels in the MBAN spectrum band. If the input value does enable a portion of those channels in the MBAN spectrum band that overlap with each other, the MLME-SET treats it as an invalid parameter and does not update the MAC parameter MacChannelEnabled and returns "Invalid Input Parameter" to the upper layer protocol. Otherwise, MLME-SET updates MacChannelEnabled to dynamically update the enabled MBAN spectrum channels that the MBAN system can access. This input value validation enables non-overlapping channels to be enabled in the MBAN spectrum band even though overlapping channels are defined within the spectrum. This is important to keep the PHY/MAC implementation complexity low since, for example, there are at most 6 channels (non-overlapping channels), instead of 30 defined overlapping channels, in the MBAN spectrum band to manage and avoid the adjacent channel interference introduced by the use of overlapping channels in the MBAN spectrum within healthcare facility.

The third channelization scheme is illustrated in FIG. 4 in which 15 overlapping channels 110 are defined to provide a good tradeoff between spectral use efficiency and implementation complexity.

Although the three channelization schemes provide the same advantages, the difference of the second and third channelization scheme from the first channelization scheme is that the non-overlapping channels in the MBAN spectrum band are not fixed and their central frequencies can be adapted to the primary user spectrum availability to achieve the best spectrum efficiency. For example, if the MBAN coordinator decides that a hospital has to avoid using the a portion of a spectrum since such spectrum is currently used by primary users, then the upper layer protocol may receive the channel use rules generated by the MBAN channel regulator and call MLME-SET to set MacChannelEnabled to enable Channel 0, 22, 27 &32, as shown in FIG. 4. The second channelization scheme can provide 4 non-overlapping channels, instead of 3 for the first channelization scheme, for in-healthcare facility deployment and achieves higher spectrum efficiency.

The second and third channelization schemes can also incorporate seamlessly with the proposed system architecture to regulate the use of MBAN spectrum channels. For in-healthcare-facility deployment, the upper layer protocol of MBAN hub devices can get the channel use rules from the MBAN channel regulator via its backhaul connection to the Healthcare IT network. The upper layer protocol uses MLME-SET primitive to set the MAC parameter MacChannelEnabled to dynamically select/enable non-overlapping channels in the MBAN spectrum band for MBAN operations. When an MBAN hub device loses its connection to the healthcare IT network, e.g. patient moving out the hospital, the MacChannelEnabled resets to its default value, with which only the overlapping channels within the MBAN spectrum band are enabled.

With reference to FIG. 5, a flowchart diagram of the operation of the MBAN system is illustrated. In a step 200, patient data is collected by one or more medical body area network (MBAN) devices. In a step 202, the one or more MBAN are prohibited from utilizing at least a portion of a predefined spectrum, part of the predefined spectrum being in use by a primary user and unavailable for use. A channelization scheme is defined with one or more channels of the predefined spectrum accessible to the one or more MBAN devices, the channelization scheme maximizing a number of channels in one or more portions of the spectrum not in use by the primary user in a step 204. In a step 206, the collected patient data is communicated from the one or more MBAN devices through a MBAN system to a hub device via short-range wireless communication. The collected patient data is communicated from the hub device to a central monitoring station via longer range wireless communication in a step 208.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A medical system comprising:
one or more medical body area network (MBAN) systems, each MBAN system including:
one or more MBAN devices configured to acquire and communicate patient data with a hub device via short-range wireless communication, the communication of the patient data via the short-range wireless communication being within a predefined spectrum, wherein part of the predefined spectrum is in use by a primary user and unavailable for use,
the hub device configured to receive patient data communicated from the one or more MBAN devices, communicates with a central monitoring station via a longer range communication;
a channel regulator configured to prohibit the one or more MBAN devices from utilizing the part of the predefined spectrum that is in use by the primary user and to define a channelization scheme with one or more channels of the predefined spectrum accessible to the one or more MBAN devices;
wherein the channelization scheme is configured to define one or more non-overlapping channels within the predefined spectrum which can only be accessed within a healthcare facility and one or more overlapping channels within the predefined spectrum which can be accessed anywhere.

2. The medical system according to claim 1, wherein the channel regulator is configured to generate channel use rules of the predefined spectrum for the one or more MBAN devices according to an authorization to use the part of the predefined spectrum received from a coordinator which provides authorizations to a plurality of healthcare facilities, monitor usage of the predefined spectrum, and report the monitored usage to the coordinator.

3. The medical system according to claim 2, wherein the channel regulator includes:
an interface configured to enable customization of the channel use rules.

4. The medical system according to claim 1, wherein the channel regulator uses a MAC parameter to dynamically enable and disable the one or more MBAN devices from transmitting on one or more of the channels within the predefined spectrum.

5. A medical system comprising:
at least one central monitoring station for monitoring a plurality of patients in each of a plurality of medical facilities;
a plurality of medical body area network (MBAN) systems each configured to be mounted to a corresponding patient and MBAN system including:
a plurality of MBAN devices configured to acquire and communicate patient data to a hub device via short-range wireless communication, wherein the MBAN devices are sufficiently low power that the short-range wireless communication is limited to within the medical facility and the communication of the patient data via the short-range wireless communication being within a predefined spectrum, wherein a part of the predefined spectrum is in use by a primary user and unavailable for use by the MBAN systems, and
the hub device configured to receive patient data communicated from the MBAN devices via the short-range wireless communication and communicate via a longer range communication to a hospital network and via the hospital network to the central monitoring station;
a channel regulator which prohibits the one or more MBAN devices from utilizing at least the part of the predefined spectrum that is unavailable for use wherein the channel regulator defines a custom channelization scheme for its medical facility for channels of the predefined spectrum available for use, by MBAN devices and communications custom channelization scheme via the hospital network;
wherein the custom channelization scheme defines overlapping channels for one portion of the parts of the predefined spectrum that is available for use by the MBAN systems and non-overlapping channels for a second portion of the predefined spectrum that is available for use by the MBAN systems.

6. The medical system according to claim 5, wherein the channelization scheme maximizes a number of channels in one or more portions of the spectrum not in use by the primary user.

7. The medical system according to claim 5, wherein the channel regulator defines a channelization scheme with one or more overlapping channels in the predefined spectrum to optimize usage of one or more available portions of the predefined spectrum by an MBAN system outside its medical facility.

8. The medical system according to claim 7, wherein a MAC parameter dynamically enables or disables access to each defined channel.

9. The medical system according to claim 5, further including:
an MBAN coordinator configured to generate keys to authorize the plurality of medical facilities to access a portion of the predefined spectrum which is available for use by the MBAN systems; and
wherein each medical facility includes one or more MBAN control points configured to receive the keys from the MBAN coordinator and convey the keys to the MBAN systems via the longer range communication.

10. A method comprising:
collecting patient data with medical body area network (MBAN) devices;
communicating the collected patient data from the MBAN devices to a hub device via short-range wireless communication, wherein the communication via short-range wireless communication is within one or more parts of a predefined spectrum that is not in use by a primary user and is available for use by the MBAN devices;
communicating the collected patient data from the hub device to a central monitoring station via longer range wireless communication;
receiving an indication of the one or more available parts and generating a channelization scheme dividing the one or more available parts into channels, wherein the channelization scheme defines one or more overlapping channels in the one or more available parts of the predefined spectrum and a MAC parameter dynamically enables or disables the MBAN devices to access to each defined overlapping channel.

11. The method according to claim 10, further including:
generating channel use rules of the predefined spectrum for the one or more MBAN devices according to monitored usage of the predefined spectrum and enabling and disabling the one or more MBAN devices from transmitting on one or more channels within the predefined spectrum according to the channel use rules.

12. The method according to claim 10, wherein the channelization scheme further defines one or more non-overlapping channels within the one or more available parts of the predefined spectrum which can only be accessed within a healthcare facility and wherein the one or more overlapping channels which can be accessed anywhere.

13. A method comprising:
collecting patient data by one or more medical body area network (MBAN) devices;
defining a channelization scheme with one or more channels of one or more parts of a predefined spectrum which are not in use by a primary user and are accessible to the one or more MBAN devices, in the channelization scheme at least a first portion of the accessible channels are overlapping and at least a second portion of the accessible channels are non-overlapping; and
prohibiting the one or more MBAN devices from utilizing the channels in one or more parts of the predefined spectrum that are in use by a primary user and unavailable for use;
communicating the collected patient data from the one or more MBAN devices through a MBAN system to a hub device via short-range wireless communication on one of the accessible channels.

14. The method according to claim 13, further including:
communicating the collected data on one of the non-overlapping channels when the patient is in a medical facility and over one of the overlapping channels when the patient is outside the medical facility.

15. The method according to claim 13, further including using a MAC parameter to disable communicating in the parts of the predefined spectrum in use by a primary user.

16. A medical system comprising:
one or more processor programmed to perform the method according to claim 10.

17. A computer readable medium containing software which when loaded into processor programs the processor to perform the method according to claim 10.

18. A medical system comprising:
one or more processor programmed to perform the method according to claim 13.

19. A computer readable medium containing software which when loaded into processor programs the processor to perform the method according to claim 13.

* * * * *